United States Patent
Laurencin et al.

(10) Patent No.: US 7,727,539 B2
(45) Date of Patent: Jun. 1, 2010

(54) POLYMERIC BIORESORBABLE COMPOSITES CONTAINING AN AMORPHOUS CALCIUM PHOSPHATE POLYMER CERAMIC FOR BONE REPAIR AND REPLACEMENT

(75) Inventors: Cato T. Laurencin, Earlysville, VA (US); Archel M. A. Ambrosio, San Diego, CA (US); Janmeet S. Sahota, New Providence, NJ (US)

(73) Assignee: Drexel University, Philadelphia, PA (US)

( * ) Notice: Subject to any disclaimer, the term of this patent is extended or adjusted under 35 U.S.C. 154(b) by 958 days.

(21) Appl. No.: 10/469,617

(22) PCT Filed: Mar. 14, 2002

(86) PCT No.: PCT/US02/07854

§ 371 (c)(1),
(2), (4) Date: Feb. 6, 2004

(87) PCT Pub. No.: WO02/071985

PCT Pub. Date: Sep. 19, 2002

(65) Prior Publication Data

US 2005/0100581 A1    May 12, 2005

Related U.S. Application Data

(60) Provisional application No. 60/275,561, filed on Mar. 14, 2001.

(51) Int. Cl.
*A61K 9/00* (2006.01)

(52) U.S. Cl. .................................... 424/400; 977/700
(58) Field of Classification Search .................. None
See application file for complete search history.

(56) References Cited

U.S. PATENT DOCUMENTS

| 5,032,552 | A | * | 7/1991 | Nonami et al. ............ 501/95.3 |
| 5,766,618 | A | | 6/1998 | Laurencin et al. |
| 5,866,155 | A | | 2/1999 | Laurencin et al. |
| 5,874,109 | A | | 2/1999 | Ducheyne et al. .......... 424/486 |
| 6,027,742 | A | * | 2/2000 | Lee et al. ................... 424/422 |
| 6,287,341 | B1 | * | 9/2001 | Lee et al. ................. 623/16.11 |
| 6,331,312 | B1 | * | 12/2001 | Lee et al. ................... 424/426 |
| 6,953,594 | B2 | * | 10/2005 | Lee et al. ................... 424/602 |

OTHER PUBLICATIONS

Devin et al., 7 J Biomater. Sci. Polymer Edn. 661 (1996).*
Skrtic et al., 53 J. Biomed Mater. Res. (Appl. Biomater.) 384 (2000).*
Antonucci, J.M. et al., "Amorphous Calcium Phosphate Based Composites: Effect of Surfactants and Poly(ethylene oxide) on Filler and Composite Properties," J. Dispers. Sci. Technol., 2007, 28(5), 819-824.
Antonios G. Mikos, et al. Laminated Three-Dimensional Biodegradable Foams For Use in Tissue Engineering, Biomaterials, 1993, vol. 14, No. 5, pp. 323-330.

* cited by examiner

*Primary Examiner*—Eric E. Silverman
(74) *Attorney, Agent, or Firm*—Woodcock Washburn, LLP

(57) ABSTRACT

A bioresorbable composite of a non-crystalline calcium phosphate ceramic synthesized within an encapsulating microspheres of bioresorbable polymeric material for use in bone repair and replacement is provided. Also provides are methods for producing these composites as well as porous, 3-dimensional scaffold produced by sintering together microspheres of this bioresorbable composite.

26 Claims, No Drawings

POLYMERIC BIORESORBABLE COMPOSITES CONTAINING AN AMORPHOUS CALCIUM PHOSPHATE POLYMER CERAMIC FOR BONE REPAIR AND REPLACEMENT

This patent application is the National Stage of International Application No. PCT/US2002/07854, filed Mar. 14, 2002, which claims the benefit of priority from U.S. Provisional Application Ser. No. 60/275,561, filed Mar. 14, 2001, each of which are herein incorporated by reference in their entirety.

This work was supported in part by the National Science Foundation (Grant No. NSG-BES9817872) and the U.S. Government has certain rights in this invention.

BACKGROUND OF THE INVENTION

With demographics shifting towards an older population and with more people living more active lifestyles, the number of orthopaedic injuries and disorders continues to rise. In the United States alone, there were more than 6 million fractures each year from 1992 to 1994 (Praemer et al. American Academy of Orthopaedic Surgeons 1999 182). In 1995, there were 216,000 total knee replacements, 134,000 total hip replacements, and close to 100,000 bone grafting procedures performed. Traditionally, autografts and allografts have been used by orthopaedic surgeons to repair fractures and other bone defects. However, limitations including donor-site morbidity, risk of disease transfer, potential immunogenicity, and insufficient supply has led investigators to search for alternative bone repair materials.

Since the main mineral component of bone is a complex calcium phosphate system called apatite, hydroxyapatite and other materials within the calcium phosphate family have been and continue to be extensively investigated (DeMaeyer et al. J. Biomed. Mater. Res. 2000 52:95-106; Keller, L. and Dollase, W. A. J. Biomed. Mater. Res. 2000 49:244-249; Zeng et al. Biomaterials 1999 20:443-451; Ma et al. J. Biomed. Mater. Res. 2001 54:284-293; and Duracan, C. and Brown, P. W. J. Biomed. Mater. Res. 2000 51:726-734). Further, calcium phosphate ceramics have been reported to be osteoconductive and to directly bond to bone (Jarcho, M. Clin. Orthop. Rel. Res. 1981 157:259-278; Kitsugi et al. Clin. Orthop. Rel. Res. 1988 234:280-290). In addition, calcium phosphate ceramics are believed to serve as precursors to bone apatite formation in vivo. Accordingly, the good bone compatibility of calcium phosphate ceramics is indicative of their suitability for repair or replacement of damaged or diseased bone. However, the brittleness of these materials limits their widespread use in orthopaedics, particularly in load-bearing applications.

Accordingly, various attempts have been made to overcome this limitation. One example has been to prepare composites of these ceramics with bioresorbable polymeric materials such as collagen and polymers of lactic acid and glycolic acid (TenHuisen et al. J. Biomed. Mater. Res. 1995 29:803-810; Yasunaga et al. J. Biomed. Mater. Res. 1999 47:412-419; Zhang et al. J. Biomed. Mater. Res. 1999 45:285-293; Devin et al. J. Biomater. Sci. Polymer. Edn. 1996 7:661-669; Boeree et al. Biomaterials 1993 14:793-796). In general, these composites are made porous in order to create a 3-dimensional scaffold that allows the ingrowth of new bone and the eventual replacement of the scaffold with new skeletal tissue (Zhang et al. J. Biomed. Mater. Res. 1999 45:285-293; Devin et al. J. Biomater. Sci. Polymer. Edn. 1996 7:661-669). In these composites, the ceramic typically comprises a calcium phosphate compound with moderate to high crystallinity (TenHuisen et al. J. Biomed. Mater. Res. 1995 29:803-810; Yasunaga et al. J. Biomed. Mater. Res. 1999 47:412-419; Zhang et al. J. Biomed. Mater. Res. 1999 45:285-293; Devin et al. J. Biomater. Sci. Polymer. Edn. 1996 7:661-669; Boeree et al. Biomaterials 1993 14:793-796).

In contrast, bone apatite is poorly crystalline and non-stoichiometric due to the presence of other ions such as magnesium and carbonate ions (Posner, A. S. and Betts, F. Acc. Chem. Res. 1975 8:273-281; Bigi et al. Calcif. Tissue Int. 1992 50:439-444). Further, crystalline forms of hydroxyapatite have been shown to resorb at a slower rate than that of new bone formation. In fact, the rate of new bone formation coincides more closely with the resorption rate of poorly crystalline or amorphous calcium phosphate ceramics (Frayssinet et al. Biomaterials 1993 14:423-429; Klein et al. J. Biomed. Mater. Res. 1983 17:769-784; Knaack et al. J. Biomed. Mater. Res. (Appl. Biomater.) 1998 43:399-409).

In the present invention, crystalline hydroxyapatite is replaced with a poorly crystalline or amorphous calcium phosphate ceramic believed to resorb concurrently with new bone growth. Also, the degradation of the amorphous calcium phosphate forms alkali products that serve to buffer the acidic degradation product of either lactic or glycolic acid in a composite of the two materials.

SUMMARY OF THE INVENTION

An object of the present invention is to provide a bioresorbable composite for use in bone repair and replacement which comprises a non-crystalline or amorphous calcium phosphate ceramic synthesized within encapsulating microspheres of a bioresorbable polymeric material.

Another object of the present invention is to provide a method for producing a bioresorbable composite which comprises a bioresorbable polymeric material and a non-crystalline or amorphous calcium phosphate ceramic for use in bone repair and replacement wherein the method comprises synthesizing the calcium phosphate ceramic within encapsulating microspheres of the bioresorbable polymeric material.

Yet another object of the present invention is to provide porous, 3-dimensional scaffolds with uniform composition throughout the scaffold, wherein said scaffolds are produced by sintering together microspheres of a non-crystalline or amorphous calcium phosphate ceramic synthesized within encapsulating microspheres of a bioresorbable polymeric material.

DETAILED DESCRIPTION OF THE INVENTION

In recent years, bioresorbable, porous, 3-dimensional scaffolds have been studied as matrices for the regeneration of tissues such as skin, cartilage and bone. The rationale for this design is that the interconnected pores allow the ingrowth of new tissue, which eventually replaces the degrading scaffold. In orthopaedic applications, the scaffolds are typically made of resorbable polymers, ceramics or composites of each.

The present invention relates to bioresorbable composites which can be sintered into 3-dimensional scaffolds for bone repair and replacement. These bioresorbable composites comprise a non-crystalline or amorphous calcium phosphate ceramic synthesized within an encapsulating microsphere of a bioresorbable polymeric material.

Calcium phosphate ceramics useful in tissue scaffolds are well known in the art. Examples of calcium phosphate ceramics which can be used in the present invention include, but are not limited to, hydroxyapatite, monocalcium phosphate, tricalcium phosphate, and tetracalcium phosphate.

Various bioresorbable, biocompatible polymers have also been created for use in medical applications. One of the most common polymers used as a biomaterial has been the polyester copolymer poly(lactic acid-glycolic acid) referred to herein as PLAGA. PLAGA is highly biocompatible, degrades into harmless monomer units and has a wide range of mechanical properties making this copolymer and its homopolymer derivatives, PLA and PGA, useful in skeletal repair and regeneration (Coombes, A. D. and Heckman, J. D. *Biomaterials* 1992 13:217-224; Mikos et al. *Polymer* 1994 35:1068-1077; Robinson et al. *Otolaryngol. Head and Neck Surg.* 1995 112:707-713; Thomson et al. *J. Biomater. Sci. Polymer Edn.* 1995 7:23-38; Devin et al. *J. Biomater. Sci. Polymer Edn.* 1996 7:661-669). In a preferred embodiment of the present invention, the bioresorbable polymeric material comprises PLAGA (50:50). However, as will be understood by those of skill in the art upon this disclosure, other polymeric materials including, but not limited to, poly(anhydrides), poly(phosphazenes), poly(orthoesters), poly(caprolactones), polyhydroxybutyrates, polyanhydroideo-imides, polypropylene fumarates, polydiaxonanes, and poly(urethanes) can also be used to form the encapsulating microspheres.

In the composites of the present invention, the calcium phosphate ceramic is synthesized within the encapsulating microspheres of the bioresorbable polymeric material. Thus, in the present invention, the microspheres serve as microreactors for the synthesis of the calcium phosphate ceramic. By carrying out the synthesis within the confined space of the microsphere's interior, crystal growth is impeded due to the constraints imposed by the small internal space of the microsphere. As a result, the formation of crystalline calcium phosphates is prevented or at least minimized. Accordingly, the calcium phosphate ceramic of the present invention more closely mimics the low crystallinity of bone apatite and thus provides a better bone substitute than a highly crystalline calcium phosphate material. In addition, amorphous or low crystalline calcium phosphates have a faster resorption rate than their crystalline counter parts, which allows them to be more readily replaced by new bone. The degradation of an amorphous calcium phosphate also forms alkali products that serve to buffer the acidic degradation products of the bioresorbable polymeric material of the microsphere. Inclusion of the bioresorbable polymeric material, however, reduces the brittleness of the ceramic component and serves to bind the microspheres together during sintering of the microspheres of this composite into tissue scaffolds. Additionally, because each individual microsphere is in itself a composite, the resulting scaffold has uniform composition throughout.

The reaction between calcium nitrate tetrahydrate and ammonium hydrogen phosphate in basic aqueous solution has been shown to produce an amorphous calcium phosphate, which becomes crystalline over time (Eanes et al. *Nature* 1965 208:365-367). In the present invention, a similar reaction was carried out within microspheres made from the bioresorbable polymer, PLAGA. Microspheres were prepared using a water-in-oil emulsion containing PLAGA, calcium nitrate tetrahydrate, and ammonium hydrogen phosphate. The water-in-oil emulsion was prepared by adding a basic aqueous solution of the nitrate and phosphate components to a solution of PLAGA in methylene chloride followed by rapid mixing. The different components of this emulsion were cooled prior to mixing in order to prevent the premature reaction of calcium nitrate with the phosphate reagent which would result in precipitation of a calcium phosphate compound at this stage of the process. Once the emulsion was made, it was added to a solution of poly (vinyl alcohol) containing an excess of calcium nitrate tetrahydrate which was being stirred with a mechanical stirrer. Excess calcium nitrate was added to minimize the diffusion of calcium ions from inside the microspheres to the surrounding solution, thereby increasing the chances of obtaining a calcium phosphate with a high Ca/P molar ratio similar to that of bone apatite, which has a Ca/P ratio of approximately 1.6 (Bigi et al. *Calcif. Tissue Int.* 1992 50:439-444). The resulting microparticles were collected after a 30-hour reaction period. These collected microparticles consisted of the composite microspheres as well as unencapsulated calcium phosphate particles. To separate the microspheres from the unencapsulated ceramic particles, the microparticle mixture was added to a hexane-water mixture, which was then shaken and allowed to stand. This separation method is based on the preference of the unencapsulated calcium phosphate particles for the aqueous layer and the preference of the microspheres for the organic layer due to the presence of the more hydrophobic PLAGA in the microspheres. The hexane layer was then collected and the microspheres isolated by filtration.

The ceramic content of the microspheres as determined by gravimetric analysis, was approximately 28%. This can be increased, however, if different mechanical properties are desired. For example, ceramic content can be increased to increase compressive modulus and other mechanical properties.

The synthesized calcium phosphate was characterized via elemental analysis to determine its Ca/P molar ratio. Tetracalcium phosphate was one of the products expected, the other being hydroxyapatite. At pH 10, which was the pH of the reaction mixture, both of these compounds are the least soluble of the various calcium phosphates and are therefore more likely to form and precipitate at this pH (Chow et al. *Mat. Res. Soc. Symp. Proc.* 1991 179:3-24). Table 1 shows the % calcium (Ca), % phosphate (P), and Ca/P ratio of the synthesized ceramic together with the calculated values for commercially available hydroxyapatite and tetracalcium phosphate.

TABLE 1

Ca and P analysis of synthesized calcium phosphate and calculated values for known calcium phosphate ceramics

| | Elemental Analysis | | |
|---|---|---|---|
| | % Ca | % P | Ca/P molar ratio |
| Synthesized calcium | 36.30 | 13.84 | 2.02 |
| Tetracalcium | 43.72 | 16.94 | 2.00 |
| Hydroxyapatite | 39.84 | 18.53 | 1.67 |

As shown, the Ca/P ratio closely matches that of tetracalcium phosphate.

The synthesized material, as well as the commercially available hydroxyapatite, were analyzed via infrared (IR). The IR spectra for both compounds were very similar except that the spectra of the synthesized calcium phosphate had peaks around 1400-1700 $cm^{-1}$ indicating the presence of carbonate. These peaks are similar to the ones observed for a carbonated apatite that was obtained after implanting brushite for 2 weeks in the femoral metaphysis of a rabbit (Constantz et al. *J. Biomed. Mater. Res.* (Appl. Biometer.) 1998 43:451-461). Since bone apatite has also been reported to contain substantial amounts of carbonate (Posner, A. S. and Betts, F. *Acc. Chem. Res.* 1975: 8:273-281), the synthesized calcium phosphate of the present invention more closely resembles the composition of bone apatite than does tetracalcium phosphate or hydroxyapatite.

To determine the crystallinity of the ceramic that was synthesized, X-ray powder diffraction (XRD) was performed. From the XRD spectra it could be seen that the hydroxyapatite was highly crystalline while the synthesized calcium phosphate material appeared non-crystalline. Further, the non-crystalline pattern was similar to those seen in other amorphous calcium phosphate XRD spectra (Eanes et al. Nature 1965 208:365-367). This non-crystalline pattern evidences the fact that by restricting the synthesis of the calcium phosphate to the small space within the microsphere's interior, crystalline formation was prevented. As discussed, bone apatite is a poorly crystalline calcium phosphate ceramic. Further, amorphous or poorly crystalline calcium phosphates are more resorbable than their crystalline counterparts. Thus, these results are indicative of the synthesized calcium phosphate ceramic of the present invention being a suitable material for bone repair when encapsulated within a bioresorbable polymeric material such as PLAGA microsphere to offset its brittleness.

The present invention also relates to 3-dimensional scaffolds produced by sintering together microspheres of a bioresorbable polymeric material and a non-crystalline calcium phosphate ceramic synthesized within the microspheres. Various conditions for sintering the microspheres can be used. Further, such conditions can be routinely determined by those of skill in the art upon reading this disclosure and based upon the melting temperature of the bioresorbable polymeric material. For example, composite microspheres comprising PLAGA were sintered at 150° C. for 1 hour in order to fuse the microspheres together. Fusion of the microspheres was possible because this sintering temperature was above the melting temperature of PLAGA. The resulting 3-dimensional scaffold was porous and did not crumble upon handling unlike some sintered, porous, calcium phosphate ceramics.

Image analysis of a cross-section of this scaffold by scanning electron microscopy showed fused microspheres and deep pores. In addition, some of the microspheres split open probably due to the slight pressure provided by the piston of the cylindrical mold assembly. As a result, the porosity of the scaffold was increased further, which also increased the surface area for cell attachment. Furthermore, the sintering process transformed the surface of the microspheres into a rougher one, characterized by the preponderance of micron-sized pores. Decades ago, the minimum pore size for effective bone ingrowth into a porous scaffold was established to be approximately 100μ (Klawitter, J. J. and Hulbert, S. F. J. Biomed. Mater. Res. Symp. 1971 2:161; Gauthier et al. Biomaterial 1998 19(1-3):133; and Daculsi, G. and Passuit, N. Biomaterials 1990 11:86). Mercury intrusion porosimetry on the scaffold indicated that a majority of the pores have diameters of at least 100μ, thus meeting the minimum requirement for bone ingrowth. Porosimetry results also showed that the scaffold had a porosity of approximately 75%.

Thus, as demonstrated herein, by restricting the reaction of a calcium salt with a phosphate compound to the small confine of a polymeric microsphere's interior, a non-crystalline, carbonated calcium phosphate ceramic useful in combination with a bioresorbable polymeric material as a composite for bone repair and replacement was obtained. Further, sintering the composite microspheres together produced a highly porous, 3-dimensional scaffold with a rough surface. In all, the combination of high-porosity and a calcium phosphate component that is non-crystalline and carbonated renders the 3-dimensional composite scaffolds produced from the composites particularly suitable for bone repair and/or replacement applications.

The following nonlimiting examples are provided to further illustrate the present invention.

EXAMPLES

Example 1

Materials

Poly(lactide-co-glycolide) or PLAGA (50:50) with a molecular weight of 50,000 was obtained from American Cyanamid. Calcium nitrate tetrahydrate, ammonium hydrogen phosphate, and concentrated ammonium hydroxide were obtained from Aldrich and used as received. Commercial hydroxyapatite used for comparison was obtained from Stryker Howmedica (Allendale, N.J.). Methylene chloride was obtained from Fisher Scientific (Camden, N.J.) and used as received.

Example 2

Preparation of Composite Microspheres

PLAGA (1.50 grams, 0.0115 mol) was dissolved in 9 mL of methylene chloride. Calcium nitrate tetrahydrate (3.54 grams, 0.0150 mole) was dissolved in 1.5 mL of water previously adjusted to pH 10 with ammonium hydroxide. In a separate vial, ammonium hydrogen phosphate (0.99 grams, 0.0075 mol) was dissolved in 2.25 mL of water, pH 10. The polymer solution and the calcium nitrate solution were kept at −70° C. prior to use, while the phosphate solution was maintained at room temperature. The cooled nitrate solution was added quickly to the cooled polymer solution followed immediately by the addition of the phosphate solution, and vortex-mixed at high speed for 20 seconds to create an emulsion. The emulsion was then poured in a slow steady stream into 600 mL of a 1% polyvinyl alcohol (PVA) solution (pH 10) containing 30 grams of calcium nitrate tetrahydrate which was being stirred at a speed of 250 rpm during the addition and was raised to 500 rpm after the addition. The reaction was allowed to proceed for 30 hours, during which ammonium hydroxide was added at regular intervals in order to maintain a pH of 10. Methylene chloride was allowed to evaporate slowly during the reaction period. After 30 hours, the hollow microspheres that floated to the top of the reaction mixture were removed using a pipette. The microparticles that settled to the bottom of the reaction vessel were collected by suction filtration and washed several times with water, pH 10. The residue was air-dried for 24 hours.

The air-dried residue was added to a separatory funnel containing 100 mL of a 50:50 mixture of water and hexane. The whole mixture was shaken and allowed to stand for a few minutes. Most of the encapsulated calcium phosphate particles settled into the lower aqueous layer while most of the microsphere stayed in the upper organic layer. The aqueous layer was removed and more water was added and the separation process was repeated. This step was repeated one more time and the microspheres in the organic layer were collected by vacuum filtration, air-dried and then lyophilized for 24 hours.

Example 3

Percent Ceramic Content

A known weight of microspheres was placed in methylene chloride to dissolve away the PLAGA component. The mixture was filtered and the residue placed in methylene chloride to remove more PLAGA. The extraction step was repeated one more time. The residue was collected, lyophilized and weighed. This experiment was performed in triplicate.

Example 4

Characterization of Synthesized Calcium Phosphate

The calcium phosphate that was synthesized within the microsphere was analyzed for calcium and phosphorus. Elemental analysis was obtained from Quantitative Technologies, Inc. (Whitehouse, N.J.). IR analysis was carried out using a Nicolet Magna IR 560 (Madison, Wis.). Powder X-ray diffraction was performed using a Siemens D500 diffractometer using Ni-filtered CuK radiation with a 2θ range from 2-60° C.

Example 5

Preparation and Characterization of 3-Dimensional Scaffold

The composite microspheres (100-250µ in diameter) were placed in a 5-mm stainless steel cylinder mold and pressed lightly with the corresponding sized piston. The whole assembly was placed in an oven at 150° C. for 1 hour in order to sinter the microspheres. A cross-section of the resulting 3-dimensional scaffold was viewed by scanning electron microscopy (SEM). Samples were gold-coated using a Denton Desk 1 sputter coater in an argon-purged chamber evacuated in 500 mTorr. The images were viewed using an Amray 1830 D4 scanning electron microscope (20 kV) with a tungsten gun and a diffusion pump. The porosity and the pore-size distribution of the scaffold was determined using a Micromeritics Autopore III Mercury Intrusion Porosimeter (Norcross, Ga.) by infusing mercury into the samples with a pressure of 40 psi. Pore size and porosity was determined as a function of pressure and corresponding mercury intrusion volume. As the mercury is forced into the pores of the sample, both the pressure necessary to move the mercury and the volume of mercury moved are recorded. From these data, both porosity and pore size are computed.

What is claimed is:

1. A bioresorbable composite comprising a bioresorbable polymeric microsphere containing approximately 28 weight percent or more of a non-crystalline calcium phosphate ceramic relative to the mass of the entire composite, wherein said non-crystalline calcium phosphate ceramic is synthesized within the encapsulating microsphere of bioresorbable polymeric material.

2. A method for producing the bioresorbable composite of claim 1 comprising synthesizing the calcium phosphate ceramic within the encapsulating microspheres of the bioresorbable material.

3. A porous, 3-dimensional scaffold comprising microspheres of the bioresorbable composite of claim 1.

4. The bioresorbable composite of claim 1, wherein the calcium phosphate is characterized by an x-ray diffraction pattern indicative of an amorphous or poorly crystalline material.

5. The bioresorbable composite of claim 1, wherein the calcium phosphate ceramic is characterized as having a stoichiometry approximately that of hydroxyapatite, calcium phosphate, tricalcium phosphate, tetracalcium phosphate, bone apatite, or any combination thereof.

6. The bioresorbable composite of claim 1, wherein the calcium phosphate is characterized as having a stoichiometry approximately that of bone apatite.

7. The bioresorbable composite of claim 1, wherein the calcium phosphate additionally comprises carbonated calcium phosphate.

8. The bioresorbable composite of claim 1, wherein the bioresorbable polymeric material comprises a polylactic acid, a polyglycolic acid, a poly(lactic acid—glycolic acid), a polyanhydride, a poly(phosphazene), a poly(orthoester), a poly(caprolactone), a polyhydroxybutyrate, a polyanhydroideco-imide, a polypropylene fumarate, a polydiaxonane, or a polyurethane polymer, or any copolymer or mixture thereof.

9. The bioresorbable composite of claim 1, wherein the bioresorbable polymeric material comprises a polylactic acid, a polyglycolic acid, a poly(lactic acid—glycolic acid) polymer or any copolymer or mixture thereof.

10. The bioresorbable composite of claim 1, wherein the bioresorbable composite is in the form of microspheres characterized as having a diameter between about 100 and about 250 microns.

11. A bioresorbable composite comprising a bioresorbable polymeric microsphere containing approximately 28 weight percent or more of a non-crystalline, poorly crystalline, or amorphous calcium phosphate ceramic relative to the mass of the entire composite.

12. The bioresorbable composite of claim 11, wherein the calcium phosphate is characterized by an x-ray diffraction pattern indicative of an amorphous or poorly crystalline material.

13. The bioresorbable composite of claim 11, wherein the calcium phosphate ceramic is characterized as having a stoichiometry approximately that of hydroxyapatite, calcium phosphate, tricalcium phosphate, tetracalcium phosphate, bone apatite, or any combination thereof.

14. The bioresorbable composite of claim 11, wherein the calcium phosphate is characterized as having a stoichiometry approximately that of bone apatite.

15. The bioresorbable composite of claim 11, wherein the calcium phosphate additionally comprises carbonated calcium phosphate.

16. The bioresorbable composite of claim 11, wherein the bioresorbable polymeric material comprises a polylactic acid, a polyglycolic acid, a poly(lactic acid—glycolic acid), a polyanhydride, a poly(phosphazene), a poly(orthoester), a poly(caprolactone), a polyhydroxybutyrate, a polyanhydroideco-imide, a polypropylene fumarate, a polydiaxonane, or a polyurethane polymer, or any copolymer or mixture thereof.

17. The bioresorbable composite of claim 11, wherein the bioresorbable polymeric material comprises a polylactic acid, a polyglycolic acid, a poly(lactic acid—glycolic acid) polymer or any copolymer or mixture thereof.

18. The bioresorbable composite of claim 11, wherein the bioresorbable composite is in the form of microspheres characterized as having a diameter between about 100 and about 250 microns.

19. The method of claim 2 wherein the bioresorbable microspheres are formed by emulsification.

20. The scaffold of claim 3 wherein the majority of pores within the scaffold are at least 100 microns in diameter.

21. The scaffold of claim 3 wherein the scaffold is suitable for tissue repair and/or replacement applications.

22. The scaffold of claim 21 wherein the tissue is bone.

23. A porous, 3-dimensional scaffold comprising microspheres of the bioresorbable composite of claim 11.

24. The scaffold of claim 23 wherein the majority of pores within the scaffold are at least 100 microns in diameter.

25. The scaffold of claim 23 wherein the scaffold is suitable for tissue repair and/or replacement applications.

26. The scaffold of claim 25 wherein the tissue is bone.

* * * * *